United States Patent [19]

Neurath et al.

[11] Patent Number: 4,877,725
[45] Date of Patent: Oct. 31, 1989

[54] IMMUNOASSAYS FOR ANTIBODIES WHICH BIND TO THE ACQUIRED IMMUNODEFICIENCY VIRUS

[75] Inventors: Alexander R. Neurath; Nathan Strick, both of New York, N.Y.

[73] Assignee: New York Blood Center, Inc., New York, N.Y.

[21] Appl. No.: 718,140

[22] Filed: Apr. 1, 1985

[51] Int. Cl.[4] .............................................. G01N 53/00
[52] U.S. Cl. ........................................... 435/5; 435/7; 435/177; 435/188; 435/195; 435/235; 435/810; 435/948; 436/506; 436/510; 436/518; 436/528; 436/531; 436/536; 436/537; 436/542; 436/543; 530/806; 530/826; 530/811; 530/812
[58] Field of Search ..................... 435/5, 7, 18, 68, 70, 435/177, 188, 195, 235–239, 948, 810; 436/506, 510, 518, 528, 531, 536, 537–540, 542, 543–545, 808–811; 530/806, 811, 812, 826

[56] References Cited

U.S. PATENT DOCUMENTS 4,520,113  5/1985  Gallo et al. ..................... 436/504
4,708,818  11/1987  Montagnier et al. ............. 435/5

OTHER PUBLICATIONS

F. Barre-Sinoussi, J. C. Chermann, F. Rey, M. T. Nugeyre, S. Chamaret, J. Gruest, C. Dauguet, C. Axler-Blin, F. Vezinet-Brun, C. Rouzinoux, W. Rozenbaum and L. Montagnier, *Science*, 220, 868 (1983).
L. Montagnier, C. Dauguet, C. Axler, S. Chamaret, J. Gruest, M. T. Nugeyre, F. Rey, F. Barre-Sinoussi and J. C. Chermann, *Ann. Virol.*, 135E, 119 (1984).
E. Vilmer, C. Rouzioux, F. Vezinet-Brun, A. Fischer, J. C. Chermann, F. Barre-Sinoussi, C. Gazengel, C. Dauguet, P. Manigne, C. Griscelli and L. Montagnier, *Lancet*, 1, 753 (1984).
R. C. Gallo, S. Z. Salahuddin, M. Popovic, G. M. Shearer, M. Kaplan, B. F. Haynes, T. J. Palker, R. Redfield, J. Oleske, B. Safai, G. White, P. Foster and P. D. Markham, *Science*, 224, 500 (1984).
J. Schupbach, M. Popovic, R. V. Gilden, M. A. Gonda, M. G. Sarngadharan and R. C. Gallo, *Science*, 224, 503 (1984).
D. Klatzmann, F. Barre-Sinoussi, M. T. Nugeyre, C. Dauguet, E. Vilmer, C. Griscelli, F. Brun-Vezinet, C. Rouzioux, J. C. Gluckman, J. C. Chermann and L. Montagnier, *Science*, 225, 59 (1984).
D. Klatzmann, E. Champagne, S. Chamaret, J. Gruest, D. Guetard, T. Hercend, J. C. Gluckman and L. Montagnier, *Nature*, 312, 767 (1984).
A. G. Dalgleish, P. C. L. Beverly, P. R. Clapham, D. H. Crawford, M. F. Greaves and R. A. Weiss, *Nature*, 312, 763 (1984).
J. A. Levy, A. D. Hoffman, S. M. Kraker, J. A. Landis, J. M. Shimabukuro and L. S. Oshiro, *Science*, 225, 840 (1984).
M. G. Sarngadharan, M. Popovic, L. Bruch, J. Schupbach and R. C. Gallo, *Science*, 224, 506 (1984).
V. S. Kalyanaraman, C. D. Cabradilla, J. P. Getchell, R. Narayanan, E. H. Braff, J. C. Chermann, F. Barre-Sinoussi, L. Montagnier, T. J. Spira, J. Kaplan, D. Fishbein, H. W. Jaffe, J. W. Curran and D. P. Francis, *Science*, 225, 321 (1984).
F. Brun-Vezinet, F. Barre-Sinoussi, A. G. Saimot, D. Christol, L. Montagnier, C. Rouzioux, D. Klatzmann, W. Rozenbaum, J. C. Gluckman and J. C. Chermann, *Lancet*, 1, 1253 (1984).
R. Cheingsong-Popov, R. A. Weiss, A. Dalgleish, R. S. Tedder, D. J. Jeffries, D. C. Shannon, R. B. Ferns, E. M. Briggs, I. V. D. Weller, S. Mi-ton, M. W. Adler, C. Farthing, A. G. Lawrence, B. G. Gazzard, J. Weber, J. R. W. Harris, A. J. Pinching, J. Craske and J. A. J. Barbara, *Lancet*, 2, 477 (1984).
B. Safai, J. E. Groopman, M. Popovic, J. Schupbach, M. G. Sarngadharan, K. Arnett, A. Sliski and R. C. Gallo, *Lancet*, 1, 1438 (1984).
S. Z. Salahuddin, P. D. Markham, R. R. Redfield, M. Essex, J. E. Groopman, M. G. Sarngadharan, M. F. McLane, A. Sliski and R. C. Gallo, *Lancet*, 2, 1418 (1984).
B. G. Gazzard, C. Farthing, D. C. Shanson, A. G. Lawrence, R. S. Tedder, R. Cheingsong-Popov, A. Dalgleish and R. A. Weiss, *Lancet*, 2, 480 (1984).
J. W. Curran, D. N. Lawrence, H. Jaffe, J. E. Kaplan, L. D. Zyla, M. Chamberland, R. Weinstein, K. J. Lui, L. B. Schoenberger, T. J. Spira, W. J. Alexander, G. Swinger, A. Ammann, S. Solomon, D. Auerbach, D.

Mildvan, R. Stoneburner, J. M. Jason, H. W. Haverkos and B. L. Evatt, *N. Engl. J. Med*, 310, 69 (1984).
P. M. Feorino, V. S. Kalyanaraman, H. W. Haverkos, C. D. Cabradilla, D. T. Warfield, H. W. Jaffe, A. K. Harrison, M. S. Gottlieb, D. Goldfinger, J. C. Chermann, F. Barre-Sinoussi, T. T. Spira, J. S. McDougal, J. W. Curran, L. Montagnier, F. A. Murphy and D. P. Francis, *Science*, 225, 69 (1984).
A. M. Hardy, J. R. Allen, W. M. Morgan and J. W. Curran, *JAMA*, 253, 215 (1985).
B. L. Evatt, D. P. Francis, M. F. McLane, T. H. Lee, C. Cabradilla, S. F. Stein, D. N. Lawrence, J. S. McDougal, T. J. Spira, J. I. Mullens and M. Essex, *Lancet*, 2, 698 (1983).
L. W. Kitchen, F. Barin, J. L. Sullivan, M. F. McLane, D. B. Brettler, P. H. Levine and M. Essex, *Nature*, 312, 367 (1984).
M. Melbye, R. J. Briggar, J. C. Chermann, L. Montagnier, S. Steinbjerg and P. Ebbesen, *Lancet*, 2, 40 (1984).
M. Melbye, R. Madhok, P. S. Sarin, G. D. O. Lowe, J. J. Goedert, K. S. Froebel, R. J. Briggar, S. Steinbjerg, C. D. Forbes, R. C. Gallo and P. Ebbesen, *Lancet*, 2, 1444 (1984).
C. Saxinger and R. C. Gallo, *Lab Invest.*, 49, 371 (1983).
F. Brun-Vezinet, C. Rouzioux, L. Montagnier, S. Chamaret, J. Gruest, F. Barre-Sinoussi, D. Geroldi, J. C. Chermann, J. McCormick, S. Mitchell, P. Piot, H. Taelman, K. B. Mirlangu, M. N. O. W. Mbendi, M. P. K. Kalambayi, C. Bridts, J. Desmyter, F. M. Feinsod and T. C. Quinn, *Science*, 226, 453 (1984).
R. S. Tedder, D. C. Shanson, D. J. Jefries, R. Cheingsong-Popov, A. Dalgleish, R. Clapham, K. Nagy and R. A. Weiss, *Lancet*, 2, 125 (1984).
S. H. Weiss, J. J. Goedert, M. G. Sarngadharan, A. J. Bodner, R. C. Gallo and W. A. Blattner, *JAMA*, 253, 221 (1985).
H. Bayer, V. Bienzle, J. Schnerde, G. Hunsman, *Lancet*, 2, 1347 (1984).
Mikulas Popovic, M. G. Sarngadharan, Elizabeth Read and Robert C. Gallo, *Science*, vol. 224, pp. 497-500, May 1984.
H. W. Jaffe, D. P. Francis, M. F. McLane, C. Cabradilla, J. W. Curran, B. W. Kilbourne, D. N. Lawrence, H. W. Haverkos, T. J. Spira, R. Y. Dodd, J. Gold, D. Armstrong, A. Ley, J. Groopman, J. Mullins, T. H. Lee and M. Essex, *Science*, pp. 1309-1312, Mar. 1984.
Jerome E. Groopman, S. Zaki Salahuddin, Mangalaseril G. Sarngadharan, James I. Mullins, John L. Sullivan, Carel Mulder, Carl J. O'Hara, Sarah H. Cheeseman, Harry Haverkos, Pierre Forgacs, Norbert Riedel, Mary F. Riedel, Mary F. McLane, Myron Essex and Robert C. Gallo, *New England Journal of Medicine*, vol. 311, No. 22, pp. 1419-1422.

*Primary Examiner*—Margaret Moskowitz
*Assistant Examiner*—Jeff P. Kushan
*Attorney, Agent, or Firm*—Sprung Horn Kramer & Woods

[57] ABSTRACT

A process for the detection of antibodies to HTLV III/LAV comprising:
 (A) mixing an unknown serum sample with a crude HTLV III/LAV viral antigen selected from the group consisting of
  (1) an antigen comprising P24 core protein and Penv protein;
  (2) a P24 antigen and
  (3) a Penv antigen,
 (B) incubating the resultant mixture from step (A);
 (C) contacting the mixture of step (B) with a solid substrate coated with antibody to HTLV III/-LAV;
 (D) incubating the mass from step (C);
 (E) washing the mass from step (D);
 (F) contacting the mass from step (E) with a labeled antibody to HTLV III/LAV;
 (G) incubating the mass from step (F);
 (H) washing the mass from step (G);
 (I) assaying the label in the mass from step (H);
 (J) as a negative control, mixing a serum sample known to be negative to HTLV III/LAV antibody with a diluent;
 (K) subjecting the mass from step (J) to steps (B) to (I);
 (L) as a positive control, mixing a predetermined amount of the crude HTLV III/LAV viral antigen and the diluent;
 (M) subjecting the mass from step (L) to steps (B) to (I); and
 (N) comparing the results of the assay for the label from steps (I), (K) and (M).

13 Claims, 5 Drawing Sheets

IMMUNOASSAYS FOR ANTIBODIES WHICH BIND TO THE ACQUIRED IMMUNODEFICIENCY VIRUS

BACKGROUND OF THE INVENTION

The present invention concerns immunoassays to antibodies to human T-lymphotropic virus (HTLV-III) [lymphadenopathy associated virus (LAV)], hereinafter referred to as "HTLV III/LAV".

Human retroviruses with tropism for a subset of T lymphocytes positive for the T4 antigen have been isolated with high frequency from individuals with the acquired immunodeficiency syndrome or from persons at high risk of developing AIDS. These viruses have been designated as human T-lymphotropic virus type III (HTLV III) or lymphadenopathy-associated virus (LAV) and are considered to be the causative agent of AIDS (F. Barre-Sinoussi, J. C. Chermann, F. Rey, M. T. Nugeyre, S. Chamaret, J. Gruest, C. Dauguet, C. Axler-Blin, F. Vezinet-Brun, C. Rouzinoux, W. Rozenbaum and L. Montagnier, *Sience*, 220, 868 (1983); L. Montagnier, C. Dauguet, C. Axler, S. Chamaret, J. Gruest, M. T. Nugeyre, F. Rey, F. Barre-Sinoussi and J. C. Chermann, *Ann. Virol.*, 135E., 119 (1984); E. Vilmer, C. Rouzioux, F. Vezinet-Brun, A. Fischer, J. C. Chermann, F. Barre-Sinoussi, C. Gazengel, C. Dauguet, P. Manigne, C. Griscelli and L. Montagnier, *Lancet*, 1, 753 (1984); R. C. Gallo, S. Z. Salahuddin, M. Popovic, G. M. Shearer, M. Kaplan, B. F. Haynes, T. J. Palker, R. Redfield, J. Oleske, B. Safai, G. White, P. Foster and P. D. Markham, *Science*, 224, 500 (1984); Schupbach, J., M. Popovic, R. V. Gilden, M. A. Gonda, M. G. Sarngadharan and R. C. Gallo, *Science*, 224, 503 (1984); M. Popovic, M. G. Sarngadharan, E. Read and R. C. Gallo, *Science*, 224, 497 (1984); D. Klatzmann, F. Barre-Sinoussi, M. T. Nugeyre, C. Dauguet, E. Vilmer, C. Griscelli, F. Brun-Vezinet, C. Rouzioux, J. C. Gluckman, J.-C. Chermann and L. Montagnier, *Science*, 225, 59 (1984); D. Klatzmann, E. Champagne, S. Chamaret, J. Gruest, D. Guetard, T. Hercend, J.-C. Gluckman and L. Montagnier, *Nature*, 312, 767 (1984); A. G. Dalgleish, P. C. L. Beverly, P. R. Clapham, D. H. Crawford, M. F. Greaves and R. A. Weiss, *Nature*, 312, 763 (1984); J. A. Levy, A. D. Hoffman, S. M. Kraker, J. A. Landis, J. M. Shimabukuro and L. S. Oshiro, *Science*, 225, 840 (1984)).

Persons infected with HTLV III/LAV usually have in their serum antibodies to one or more viral proteins (Barre-Sinoussi et al., supra; M. G. Sarngadharan, M. Popovic, L. Bruch, J. Schupbach and R. C. Gallo, *Science*, 224, 506 (1984); Levy et al., supra; V. S. Kalyanaraman, C. D. Cabradilla, J. P. Getchell, R. Narayanan, E. H. Braff, J.-C. Chermann, F. Barre-Sinoussi, L. Montagnier, T. J. Spira, J. Kaplan, D. Fishbein, H. W. Jaffe, J. W. Curran and D. P. Francis, *Science*, 225, 321 (1984); F. Brun-Vezinet, F. Barre-Sinoussi, A. G. Saimot, D. Christol, L. Montagnier, C. Rouzioux, D. Klatzmann, W. Rozenbaum, J. C. Gluckmann and J. C. Chermann, *Lancet*, 1, 1253 (1984); R. Cheingsong-Popov, R. A. Weiss, A. Dalgleish, R. S. Tedder, D. J. Jeffries, D. C. Shannon, R. B. Ferns, E. M. Briggs, I. V. D. Weller, S. Mitton, M. W. Adler, C. Farthing, A. G. Lawrence, B. G. Gazzard, J. Weber, J. R. W. Harris, A. J. Pinching, J. Craske and J. A. J. Barbara, *Lancet*, 2, 477 (1984); B. Safai, J. E. Groopman, M. Popovic, J. Schupbach, M. G. Sarngadharan, K. Arnett, A. Sliski and R. C. Gallo, *Lancet*, 1, 1438 (1984)), but such antibodies are not always detectable in infected persons (S. Z. Salahuddin, P. D. Markham, R. R. Redfield, M. Essex, J. E. Groopman, M. G. Sarngadharan, M. F. McLane, A. Sliski and R. C. Gallo, *Lancet*, 2, 1418 (1984); B. G. Gazzard, C. Farthing, D. C. Shanson, A. G. Lawrence, R. S. Tedder, R. Cheingsong-Popov, A. Dalgleish and R. A. Weiss, *Lancet*, 2, 480 (1984)).

HTLV III/LAV is rarely transmitted by blood transfusion (J. W. Curran, D. N. Lawrence, H. Jaffe, J. E. Kaplan, L. D. Zyla, M. Chamberland, R. Weinstein, K.-J. Lui, L. B. Schoenberger, T. J. Spira, W. J. Alexander, G. Swinger, A. Ammann, S. Solomon, D. Auerbach, M. Mildvan, R. Stoneburner, J. M. Jason, H. W. Haverkos and B. L. Evatt, *N. Engl. J. Med.*, 310, 69 (1984); H. W. Jaffe, D. P. Francis, M. F. McLane, C. Cabradilla, J. W. Curran, B. W. Kilbourne, D. N. Lawrence, H. W. Haverkos, T. J. Spira, R. Y. Dodd, J. Gold, D. Armstrong, A. Ley, J. Groopman, J. Mullins, T. H. Lee and M. Essex, *Science*, 223, 1309 (1984); P. M. Feorino, V. S. Kalyanaraman, H. W. Haverkos, C. D. Cabradilla, D. T. Warfield, H. W. Jaffe, A. K. Harrison, M. S. Gottlieb, D. Goldfinger, J.-C. Chermann, F. Barre-Sinoussi, T. T. Spira, J. S. McDougal, J. W. Curran, L. Montagnier, F. A. Murphy and D. P. Francis, *Science*, 225, 69 (1984); J. E. Groopman, S. Z. Salahuddin, M. G. Sarngadharan, J. I. Mullins, J. L. Sullivan, C. Mulder, C. J. O'Hara, S. H. Cheeseman, H. Haverkos, P. Forgacs, N. Riedel, M. F. McLane, M. Essex and R. C. Gallo, *N. Engl. J. Med.*, 311, 1419 (1984); A. M. Hardy, J. R. Allen, W. M. Morgan and J. W. Curran, *JAMA*, 253, 215 (1985), and much more frequently by products prepared from pooled human plasma (Vilmer et al., supra; Popovic et al., supra; Cheingsong-Popov et al., supra; B. L. Evatt, D. P. Francis, M. F. McLane, T. H. Lee, C. Cabradilla, S. F. Stein, D. N. Lawrence, J. S. McDougal, T. J. Spira, J. I. Mullens and M. Essex, *Lancet*, 2, 698 (1983); L. W. Kitchen, F. Barin, J. L. Sullivan, M. F. McLane, D. B. Brettler, P. H. Levine and M. Essex, *Nature*, 312, 367 (1984); M. Melbye, R. J. Briggar, J. C. Chermann, L. Montagnier, S. Steinbjerg and P. Ebbesen, *Lancet*, 2, 40 (1984); M. Melbye, R. Madhok, P. S. Sarin, G. D. O. Lowe, J. J. Goedert, K. S. Fraebel, R. J. Briggar, S. Stenbjerg, C. D. Forbes, R. C. Gallo and P. Ebbesen, *Lancet*, 2, 1444 (1984)), as indicated by the high prevalence of anti-HTLV III/-LAV antibodies in hemophiliacs. The risk of HTLV III/LAV transmission has indicated the need for screening of blood donors for markers of infection with this human retrovirus(es). Since detection of viral markers (antigens, reverse transcriptase or specific nucleotide sequences) produced by in vitro replicating T lymphocytes, isolated from individual donors, is prohibitively cumbersome for screening purposes, the assay methods have to be based on the presence of antigens or antibodies in serum. Individuals who have been infected with HTLV III or LAV viruses generally may be identified on the basis of a positive serological test for antibodies against the protein components of these viruses. Purified viruses or viral proteins have been heretofore utilized for developing such tests.

The following methods for detection of antibodies to HTLV III/LAV-specific proteins have been developed: (1) an ELISA assay in which wells of polystyrene plates coated with detergent-disrupted purified virus are used, and the presence of antibodies reacting with virus proteins is detected by enzyme-labeled anti-human IgG (C. Saxinger and R. C. Gallo, *Lab. Invest.*, 49, 371 (1983); Sarngadharan et al., supra; Brun-Vezinet et al., supra); (2) Western blot analyses in which viral proteins separated by electrophoresis are transferred to strips of nitrocellulose and reacted with serum specimens; the attached antibodies are subsequently detected with $^{125}$I-labeled anti-human IgG (Schupback et al., supra; Safai et al., supra); (3) a radioimmunoprecipitation test (RIPA), followed by polyacrylamide gel electrophoresis which detects antibodies to [$^{35}$S]-labeled viral proteins (F. Brun-Vezinet, C. Rouzioux, L. Montagnier, S. Chamaret, J. Gruest, F. Barre-Sinoussi, D. Geroldi, J. C. Chermann, J. McCormick, S. Mitchell, P. Piot, H. Taelman, K. B. Mirlangu, M. N. O. W. Mbendi, M. P. K. Kalambayi, C. Bridts, J. Desmyter, F. M. Feinsod and T. C. Quinn, *Science*, 226, 453 (1984); Kitchen et al., supra); (4) a RIPA test with $^{125}$I-labeled purified LAV core protein P25 (Kalyanaraman et al., supra); (5) an indirect living cell immunofluorescence test of HTLV III-infected cells (Evatt et al., supra; Kitchen et al., supra; Cheingsong-Popov et al., supra); and (6) a competitive RIA test utilizing human anti-HTLV III IgG on a solid support, the same IgG labeled with $^{125}$I, and a crude extract from HTLV III-infected cells (R. S. Tedder, D. C. Shanson, D. J. Jefries, R. Cheingsong-Popov, A. Dalgleish, P. Clapham, K. Nagy and R. A. Weiss, *Lancet*, 2, 125 (1984); Cheingsong-Popov et al., supra).

Methods (1) and (4) above require either purified virus or a purified isolated viral protein. Virus purification, however, generally involves elaborate, expensive and potentially hazardous virus purification steps. Methods (5) and (6) above are based on the use of infected cells.

For a better understanding of the natural history of HTLV III/LAV infections, it seems important to follow the appearance in serum of antibodies to distinct viral proteins. Methods (2) and (3) above are ideally suited for that purpose. However, these methods are too complex for routine screening purposes. Therefore, simpler direct RIA or ELISA methods for antibodies to distinct epitopes of HTLV III/LAV structural components would be of great value.

Using the double-antibody test (Saxinger and Gallo, supra), proposed for routine screening, 93% of healthy blood donors were negative, 6% appeared borderline positive and 1% appeared positive for anti-HTLV III (S. H. Weiss, J. J. Goedert, M. G. Sarngadharan, A. J. Bodner, R. C. Gallo and W. A. Blattner, *JAMA*, 253, 221 (1985). This necessitated further confirmatory tests by Western blot analysis, which demonstrated that in most cases of healthy donors, the ELISA-positive samples were actually negative for anti-HTLV III. When other assays were utilized, the prevalence of anti-HTLV III/LAV-positives among healthy donors, not belonging to the high-risk groups of developing AIDS, was 1/298 by indirect membrane immunofluorescence (Jaffe et al., supra), 0/259 by RIPA with $^{125}$I-labeled LAV core protein (Kalyanaraman et al., supra) and 0/1,000 by a competitive RIA utilizing $^{125}$I-labeled anti-HTLV III/LAV (Cheingsong-Popov et al., supra).

SUMMARY OF THE INVENTION

It is an object of the present invention to provide less expensive and more specific tests to screen blood donors for individuals who have been infected with HTLV III/LAV.

It is another object of the present invention to screen individuals for acquired immunodeficiency syndrome associated virus using RIA and ELISA assays which (a) obviate the need for purified virus or virus proteins, (b) do not utilize infected cells and thus do not diminish the source for continuous production of viral antigens and (c) are specific for individual major virus proteins, namely, a major core protein of HTLV III/LAV, which will be dsignated hereinafter as P24, and the envelope proteins of HTLV III/LAV, which will be disignated hereinafter as Penv.

It is a further object of the invention to drastically decrease non-specific reactions in tests for HTLV III/LAV.

It is still another object of the present invention to prepare crude HTLV III/LAV viral antigens.

The above objects and other objects are realized in the present invention.

The present invention provides for tests for anti-HTLV III/LAV which (1) do not require purified virus as one of the reagents; (2) make use of viral antigens present in tissue culture medium in addition to mature virus particles; such antigens may either be synthesized in excess over the amounts needed for virus assembly, or they may be released from virus particles as the result of virus degradation; (3) are not to be based on the detection of antibodies by using anti-human IgG, since false positive results may be obtained in such tests with some specimens, independently of the antigen used to coat polystyrene plates.

The present invention concerns a process for preparing a crude HTLV III/LAV viral antigen comprising:

(i) propagating HTLV III/LAV virus infected cells in a culture medium containing fetal calf serum;

(ii) separating the cells out of the medium of step (i);

(iii) precipitating proteins and virus out from the resultant medium of step (ii); and (iv) inactivating and disrupting (dissociating) the virus from the product of step (iii) and releasing individual virus components including P24 and Penv.

The present invention concerns a process for preparing P24 antigen comprising:

(i) propagating HTLV III/LAV virus infected cells in a culture medium containing fetal calf serum;

(ii) separating the cells out of the medium of step (i);

(iii) precipitating proteins and virus out from the resultant medium of step (ii); and (iv) inactivating and disrupting (dissociating) the virus from the product of step (iii), (v) separating out (such as by molecular exclusion chromatography, e.g., by Sephadex G-75 chromatography) P24 antigen.

The present invention also relates to a process for preparing Penv antigen comprising:

(i) propagating HTLV III/LAV virus infected cells in a culture medium containing fetal calf serum;

(ii) separating the cells out of the medium of step (i);

(iii) precipitating proteins and virus out from the resultant medium of step (ii); and (iv) inactivating and disrupting (dissociating) the virus from the product of step (iii), (v) separing out (such as by molecular exclusion chromatography, e.g., by Sephadex G-75 chromatography) Penv antigen, which include P24 recovered in void volume column fractions.

The present invention also relates to a process for the detection of antibodies to HTLV III/LAV comprising:

(a) mixing an unknown serum sample with the crude HTLV III/LAV viral antigen prepared as described above diluted in a diluent, for example, 10% normal human serum and 10% fetal calf serum;

(b) incubating the resultant mixture from step (a);

(c) contacting the resultant mixture of step (b) with a solid substrate coated with antibody to HTLV III/-LAV;

(d) incubating the resultant mass from step (c);

(e) washing the resultant mass from step (d);

(f) contacting the resultant mass from step (e) with a radiolabeled or enzyme antibody to HTLV III/LAV;

(g) incubating the resultant mass from step (f);

(h) washing the resultant mass from step (g);

(i) subjecting the resultant mass from step (h) to gamma-counting (when radiolabeled antibody is used) or ELISA (if enzyme labeled antibody is used);

(j) as a negative control, mixing a serum sample known to be negative to HTLV III/LAV antibody with a diluent comprising fetal calf serum, human serum and a buffer;

(k) subjecting the resultant mass from step (j) to steps (b) to (i);

(l) as a positive control, mixing a predetermined amount of crude HTLV III/LAV viral antigen prepared according to the procedure described above and the diluent as described above in step (j);

(m) subjecting the resultant mass from step (l) to steps (b) to (i); and (n) comparing the counts or enzymatic activity from steps (i), (k) and (m).

The present invention relates to a process for the detection of anti-P24 antibodies of HTLV III/LAV comprising:

(a) mixing P24 antigen, such as P24 antigen prepared as described above, with an unknown serum sample diluted in a diluent, for example, 10% normal human serum and 10% fetal calf serum;

(b) incubating the resultant mixture from step (a);

(c) contacting the resultant mixture of step (b) with a solid substrate coated with antibody to HTLV III/-LAV;

(d) incubating the resultant mass from step (c);

(e) washing the resultant mass from step (d);

(f) contacting the resultant mass from step (e) with a radiolabeled or enzyme antibody to HTLV III/LAV;

(g) incubating the resultant mass from step (f);

(h) washing the resultant mass from step (g);

(i) subjecting the resultant mass from step (h) to gamma-counting (when radiolabeled antibody is used) or ELISA (if enzyme labeled antibody is used);

(j) as a negative control, mixing a serum sample known to be negative to HTLV III/LAV antibody with a diluent comprising fetal calf serum, human serum and a buffer;

(k) subjecting the resultant mass from step (j) to steps (b) to (i);

(l) as a positive control, mixing a predetermined amount of P24 antigen and the diluent as described above in step (j);

(m) subjecting the resultant mass from step (l) to steps (b) to (i); and (n) comparing the counts or enzymatic activity from steps (i), (k) and (m).

The present invention concerns a process for the detection of anti-Penv antibodies of HTLV III/LAV comprising:

(a) mixing Penv antigen, such as Penv antigen prepared as described above;

(b) incubating the resultant mixture from step (a);

(c) contacting the resultant mixture of step (b) with a solid substrate coated with antibody to HTLV III/-LAV;

(d) incubating the resultant mass from step (c);

(e) washing the resultant mass from step (d);

(f) contacting the resultant mass from step (e) with a radiolabeled or enzyme antibody to HTLV III/LAV;

(g) incubating the resultant mass from step (f);

(h) washing the resultant mass from step (g);

(i) subjecting the resultant mass from step (h) to gamma-counting (when radiolabeled antibody is used) or ELISA (if enzyme labeled antibody is used);

(j) as a negative control, mixing a serum sample known to be negative to HTLV III/LAV antibody with a diluent comprising fetal calf serum, human serum and a buffer;

(k) subjecting the resultant mass from step (j) to steps (b) to (i);

(l) as a positive control, mixing a predetermined amount of Penv antigen and the diluent as described above in step (j);

(m) subjecting the resultant mass from step (l) to steps (b) to (i); and (n) comparing the counts or enzymatic activity from steps (i), (k) and (m).

The present invention concerns another process for detection of antibodies to HTLV III/LAV comprising:

(a) contacting a solid substrate coated with antibody to HTLV III/LAV with crude HTLV III/LAV viral antigen prepared as described above;

(b) incubating the resultant mixture from step (a);

(c) washing the resultant mass from step (b);

(d) contacting the resultant mixture of step (c) with radiolabelled or enzyme labelled antibody to HTLV III/LAV and an unknown serum specimen;

(e) incubating the resultant mass from step (d);

(f) washing the resultant mass from step (e);

(g) determining the radioactivity or enzymatic activity of the resultant mass from step (f).

The present invention also concerns a process for the detection of anti-P24 antibodies to HTLV III/LAV comprising:

(a) contacting a P24 antigen with a solid substrate coated with antibody to HTLV III/LAV;

(b) incubating the resultant mixture from step (a);

(c) washing the resultant mass from step (b);

(d) contacting the resultant mixture of step (c) with a radiolabelled or enzyme labelled antibody to HTLV III/LAV and an unknown serum specimen;

(e) incubating the resultant mass from step (d);

(f) washing the resultant mass from step (e);

(g) determining the radioactivity or enzymatic activity of the resultant mass from step (f).

The present invention further concerns a process for the detection of antibodies to HTLV III/LAV comprising:

(a) contacting a Penv antigen with a solid substrate coated with antibody to HTLV III/LAV;

(b) incubating the resultant mixture from step (a);

(c) washing the resultant mass from step (b);

(d) contacting the resultant mixture of step (c) with a radiolabelled or enzyme labelled antibody to HTLV III/LAV and an unknown serum specimen;

(e) incubating the resultant mass from step (d);

(f) washing the resultant mass from step (e);

(g) determining the radioactivity or enzymatic activity of the resultant mass from step (f).

The present invention also relates to a diagnostic test kits for detecting antibodies to HTLV III/LAV virus in a test sample, comprising:

(a) a solid substrate having adsorbed thereon antibodies to HTLV III/LAV;

(b) a given amount of radiolabeled or enzyme labeled antibody to HTLV III/LAV;

(c) an extract of the crude HTLV III/LAV viral antigen prepared as described above, or P24 antigen, such as P24 antigen prepared as described above, or Penv antigen, such as Penv antigen prepared as described above;

(d) a negative control containing normal human sera known to be negative to HTLV III/LAV antibody;

(e) a positive control containing human sera known to be positive to HTLV III/LAV antibody.

The tissue culture medium described above contains in addition to natural virions, both P24 and Penv proteins in unassembled forms. The procedures of the present invention make use of these unassembled viral components (P24 and Penv), in addition to releasing additional P24 and Penv by disruption of the virus. Prior to the present invention, the unassembled P24 and Penv was discarded and only intact purified virus was utilized in designing tests for anti-HTLV III/LAV.

BRIEF DESCRIPTION OF THE DRAWINGS

FIG. 5 is similar to the actual plot in FIG. 2. FIG. 5 depicts the results attainable by molecular exclusion chromatography on Sephadex G-75 of HTLV III antigens prepared as described for FIG. 1, but using lower dilutions in order to discern two peaks, namely Peak I corresponding to Penv and Peak II corresponding to P24. The area under the graph from point c to point d is the P24 antigen and represents approximately 95% of the total antigen. The area under graph from point a to point b is Penv antigens and represents approximately 5% of the total antigens. It is preferred that a separation for Penv be made to include the area under the graph from point a to point b in order to exclude the transition zone that extends from point b to point c.

DETAILED DESCRIPTION OF THE INVENTION

Figure 1:
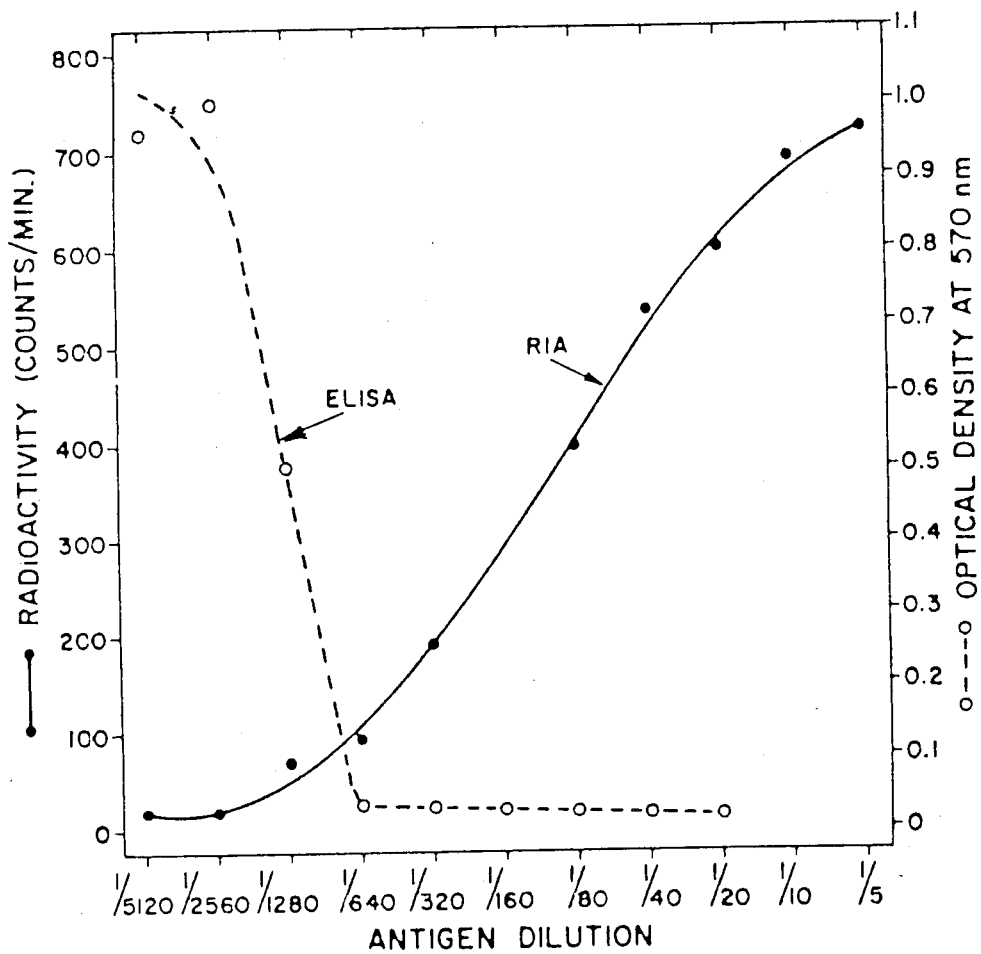
FIG. 1 is a plot of antigen dilution vs. radioactivity showing the results of RIA tests and antigen dilution vs. optical density showing the results of ELISA tests of serial dilutions in tris buffered saline (TS) containing 10% of each normal human and fetal bovine serum of an HTLV III-infected tissue culture derived fraction, obtained by precipitation with 7% PEG 6000 and by subsequent treatment with 1 mg/ml each of Tween 80 and TNBP. It is noted that optical density readings corresponding to the ELISA test decrease with increasing amounts of antigen; this is due to the fact that beta-lactamase activity measurements are based on decolorization of the substrate. Control preparations isolated from non-infected tissue culture medium were negative in these assays.

Screening for antibodies to HTLV III/LAV is facilitated by the present invention which involves assays based on the use of crude virus-infected tissue culture media, thus avoiding elaborate, expensive and potentially hazardous virus purification steps. In a preferred embodiment of the present invention serum specimens are mixed with an appropriate dilution of an HTLV III-infected tissue culture derived fraction, obtained by precipitation with polyethylene glycol 6000 and treated with viral disruptive agents comprising a wetting agent such as polyoxyethylene derivatives of fatty acid partial esters of sorbitol anhydrides, e.g., "Tween 20", and preferably "Tween 80" and a solvent such as tri-alkyl phosphate, wherein said alkyl groups contain 4 to 10 carbon atoms, e.g., tri-(n-butyl) phosphate, tri-(n-hexyl) phosphate, tri-(2-ethylhexyl) phosphate, tri-(n-decyl) phosphate, and preferably tri-n-butylphosphate, and incubated with polystyrene beads coated with antibodies to HTLV III/LAV (anti-HTLV III). Other viral disruptive agents can be employed in the present invention, such as, for example, ether and ether and a non-ionic detergent. Non-limiting examples of such ethers and detergents and conditions for the use of same as virus inactivating agents are described in U.S. Pat. No. 4,481,189, the entire contents of which are incorporated by reference herein. Conditions for virus disruption (viral inactivation and dissociation) are described in U.S. Pat. No. 3,962,421, the entire contents of which are incorporated by reference herein.

Washed beads used in the present invention can be incubated with either $^{125}I$ or beta-lactamase-labeled anti-HTLV III. The radioactivity or enzymatic activity associated with the beads was found to be proportional to the quantity of HTLV III antigen originally added to the beads. Applicants found that the presence of anti-HTLV III in serum specimens added to HTLV III/LAV antigen preparations resulted in decreased antigen binding and thus in decreased radioactivity or diminished beta-lactamase activity associated with the beads and that the test was specific for antibodies to the approximately 24 kD core protein of HTLV III using sufficiently diluted antigen.

The assays of the present invention differ from heretofore competitive RIA assays in the following respects: (1) tissue culture medium, rather than infected cells is the source of antigen(s); (2) the assay is not a competitive RIA, but is based on the inhibition of the attachment of HTLV III antigen(s) to anti-HTLV III-coated beads (or wells) by antibodies in the specimens. The latter test configuration increases the sensitivity of antibody detection about 5-fold as compared with competitive RIA, and (3) the tests are operationally specific for the P24 core antigen.

Although a crude HTLV III antigen preparation is utilized in the assays of the present invention, they are operationally specific for antibodies to the core protein P24, since the latter vial component appears to be the most abundant antigen in tissue culture medium recognized by human anti-HTLV III/LAV, in agreement with observation of Vilmer et al. supra and Brun-Vezinet and Chamaret et al. supra. Thus, the assays described herein appear to represent the most straightforward approach for screening distinct human populations for antibodies to the HTLV III/LAV major core protein, since other assays depend on the availability of labeled purified P24 (Kalyanaraman et al. supra; Brun-Vezinet and Chamaret et al. supra). Penv has to be separated from P24 in order to design tests specific for anti-Penv.

The assays described herein discriminate between a normal control population and distinct groups at high risk of developing AIDS in whom the prevalence of detectable anti-HTLV III P24 antibodies is 76 to 212 times higher than in controls (see the Table herein). The prevalence of these antibodies correlates with the presence of chronic lymphadenopathy, in agreement with results using other assays (Brun-Vezinet and Saimot et al., supra; Safai et al., supra,; Cheingsong-Popov et al., supra; H. Bayer, V. Bienzle, Schnerde, J., Hunsman, G., Lancet, 2, 1347 (1984)).

The incubation steps required in carrying out the invention can be effected in a known manner, such as by incubation at temperatures of between about 20° C. and about 50° C. for between about 1 hour and about 30 hours.

Washings are typically effected using an aqueous solution such as one buffered at a pH of 6–8, preferably at a pH of about 7, employing an isotonic saline solution.

Non-limiting examples of suitable solid supports for use in the present invention include polystyrene beads, filter paper, test tubes and microtiter plates.

Non-limiting examples of enzymes for use in the present invention include beta-lactamase, catalase, peroxidase, urease, glucose oxidase, alkaline phosphatase and horseradish peroxidase.

EXAMPLES

Example 1

RIA and ELISA tests for an HTLV III antigen and characterization of the antigen

In attempts to select the best available source of antibodies for the development of immunoassays for HTLV III, IgG was isolated from sera of several homosexual male donors with lymphadenopathy using DEAE-cellulose chromatography. Each of the IgG's was used to develop an RIA test.

The isolated IgG was used to coat polystyrene beads or 96-well plates (Removawell strips; Immulon II, Dynatech Laboratories, Alexandria, Va.) as described by A. R. Neurath, in *Methods in Enzymology*, 73, J. J. Langone and H. Van Vunakis, eds., Academic Press, New York, pp. 127–138 (1981). IgG was labeled with $^{125}I$ using Iodobeads (Pierce Chemical Company, Rockford, Ill.) following the manufacturer's instructions. Conjugation of IgG with beta-lactamase was performed as described by Yolken et al., S.-B. Wee and M. Van Regenmortel, *J. Immunol. Meth.*, 73, 109 (1984).

The crude HTLV III antigen was prepared as follows: HTLV III was propagated in the H9 T-cell line as described in M. Popovic et al., supra. Tissue culture fluids after removal of cells by low speed centrifugation, were mixed with 0.304 volumes of a solution of polyethylene glycol 6000 (PEG 6000; 300 g/liter). The precipitate, containing approximately 85% of HTLV III antigens originally present in the medium (as determined by RIA), was separated by centrifugation and redissolved in 1/20 volume of the original tissue culture fluid by 0.14M NaCl-0.01M Tris, 0.02% $NaN_3$, pH 7.2 (TS). Tween 80 and tri-n-butylphosphate (TNP) were each added to a final concentration of 1 mg/ml and the mixture was incubated overnight at 37° C. to disrupt the virus particles (A. R. Neurath et al., *J. Gen. Virol.*, 14, 33 (1972); U.S. Pat. No. 3,962,421). The final product was stored at 4° C. After one month, no loss of antigenic activity was observed under these conditions.

For RIA tests of HTLV III antigens, 400 µl of serial dilutions of the crude antigen, prepared as described above, in TS containing 10% (v/v) of each normal human serum and fetal bovine serum (TS-HB) were incubated overnight at room temperature with anti-HTLV III-coated beads. The beads were washed with TS, incubated with 400 µl of $^{125}I$-labeled anti-HTLV III (equivalent to $10^5$ cpm) in TS-HB for 2 hours at 37° C., washed with TS and counted in a gamma-counter.

The IgG which yielded the most sensitive test for HTLV III antigens present in dilutions of a crude preparation was selected for all additional studies. The results using this IgG are shown in FIG. 1.

Since ELISA tests are preferable to RIA tests for screening of many specimens, if the assay sensitivity is not compromised, the selected IgG was also conjugated with beta-lactamase. This enzyme was selected on the basis of preliminary experiments with antibodies to hepatitis B surface antigen (anti-HBs), which demonstrated that anti-HBs-beta-lactamase conjugates retain more antibody activity than conjugates with other enzymes used in ELISA (i.e. beta-galactosidase, peroxidase or alkaline phosphatase).

ELISA tests were performed under similar conditions as the above-described RIA tests, except that wells of Removawell plates were used instead of polystyrene beads, and the volume of samples was reduced to 200 µl. The anti-HTLV III-beta-lactamase conjugate was used at a dilution (in TS-HB) corresponding to a final concentration of 240 ng IgG per ml (=48 ng IgG per well). Beta-lactamase activity was measured on the basis of decolorization of a starch-iodine mixture (Yolken et al. supra). Two hundred microliters of the substrate solution (1 mg/ml of soluble starch, 15 µg/ml of penicillin G, 30 µg/ml of $I_2$ and 0.8 mg/ml of KI in 0.14M NaCl, 0.05M phosphate, pH 7.2) were added per well. After 1 hour at 20° C., the optical density (OD at 570 nm) of samples was read automatically with MR 600 Microplate Reader (Dynatech). Results of ELISA and RIA tests were corrected for O.D. readings or counts obtained with control samples (C−) containing diluent only.

Anti-HTLV III was detected by RIA- or ELISA-inhibition tests. Five hundred microliters of samples (200 μl for ELISA) containing HTLV III antigen at a final 1:100 dilution (see FIG. 1) and serum specimens at a final 1:10 dilution in TS-HB were incubated 30 minutes at 37°, followed by 1 hour at 20° C. The mixtures were added to polystyrene beads (RIA) or plates (ELISA) and residual HTLV III antigen(s) was detected as described above. Controls included samples without antigen (C−) and samples with antigen containing normal human serum in the diluent (C+). Those samples for which radioactive counts or OD readings ($C_x$) fulfilled the condition $[C_x-C-] \leq \frac{1}{2}[C+-C-]$ were considered positive for antibodies.

The resulting ELISA test for HTLV III appeared as sensitive as the RIA test (endpoint dilution of antigen for both tests ≈1/1280; FIG. 1). As shown in in FIG. 1, optical density readings corresponding to the ELISA test decreased with increasing amounts of antigen due to the fact that beta-lactamase activity measurements were based on decolorization of the substrate. Control preparations isolated from non-infected tissue culture medium were negative in these assays.

The RIA test appeared more suitable for precise antigen quantitation, since trace amounts of beta-lactamase cause complete decolorization of the substrate, and the substrate spontaneously decolorizes slowly. However, test results can easily be determined by eye and permanent records can be obtained by making a copy of the 96-well plate using a standard office photocopier (Yolken et al., supra).

Molecular exclusion chromatography of the HTLV III preparation was performed using K15/30 columns containing Sephadex G-75 (50 ml; Pharmacia Fine Chemicals, Piscataway, N.J.). Blue dextran, chymotrypsinogen A (molecular weight=25,000) and cytochrome C (molecular weight=12,400) served as markers for column calibration. The elution buffer was 0.5M NaCl, 0.01M Tris, 0.02% NaN$_3$, pH 7.2. One ml fractions were collected. Fractions were tested by RIA at a 1:50 dilution and the relative amount of antigen detected was calculated from the calibration curve shown in FIG. 1.

Figure 2:
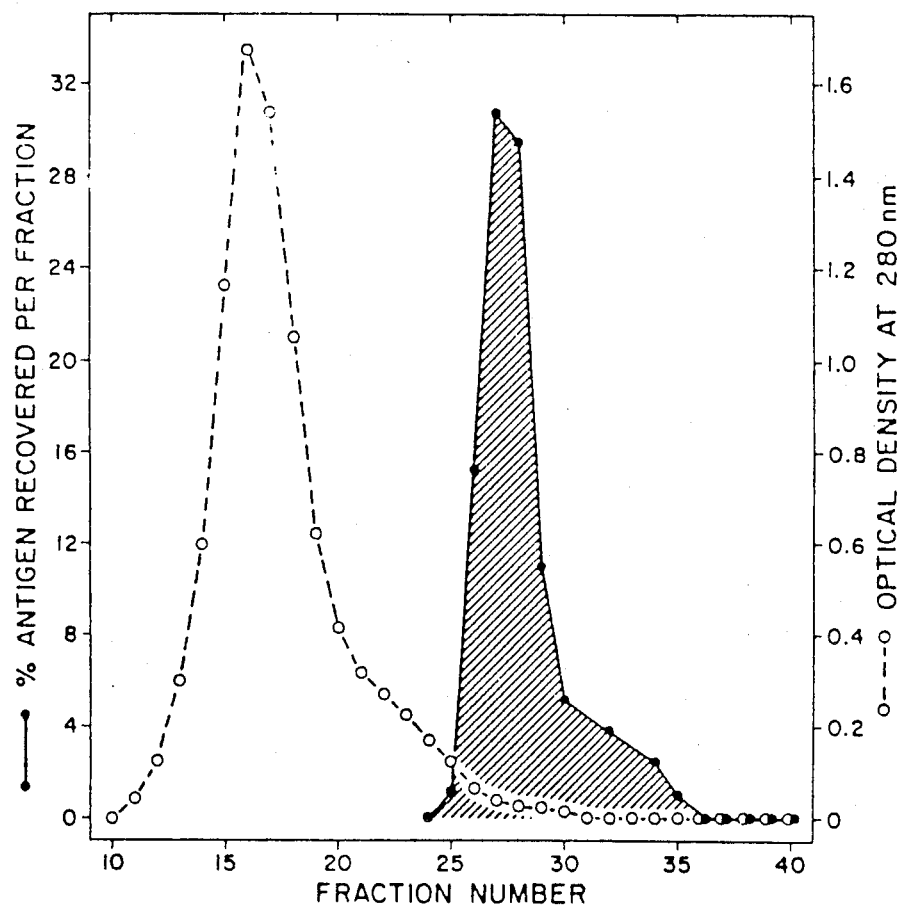
FIG. 2 depicts a plot of fraction number vs. antigen recovered per fraction and fraction number vs. optical density showing the results of molecular exclusion chromatography on Sephadex G-75 of HTLV III antigens (prepared as described for FIG. 1). One ml fractions were collected. Fractions were tested by RIA at a 1:50 dilution and the relative amount of antigen detected was calculated from the calibration curve show in FIG. 1.

As shown in FIG. 2, molecular exclusion chromatography of the HTLV III preparation resulted in the separation of the major portion of antigen from the bulk of proteins precipitated from the tissue culture medium by PEG 6000 (70 mg/ml). The peak of antigen activity corresponded to a molecular weight of 25 kD, as established by separate chromatography of molecular weight markers on the same column. Fractions 25–35 were pooled, concentrated and submitted to Western blot analysis performed as described by A. R. Neurath, et al., *Science*, 224, 392 (1984), except that 8M urea was omitted from both sample and electrophoresis buffers. A single band corresponding to a moleclar weight of 23.4 kD was discerned. In agreement with the proposed nomenclature (J. Schupbach et al., supra), the antigen detected after molecular exclusion chromatography (FIG. 2) or by Western blots was designated at P24. When fractions after chromatography were retested at a lower dilution (1:1), an additional antigen(s), i.e., Penv. became detectable in the void volume of the column, representing less than 5% of input antigen.

Isoelectric focusing of HTLV III antigens (prepared as described for FIG. 1) was performed as described in A. R. Neurath, et al. 1975, *J. Gen. Virol.*, 27, 8 (1975). Fractions were tested by RIA at a 1:10 dilution and the relative amount of antigen detected was calculated from the calibration curve shown in FIG. 1.

Figure 3:
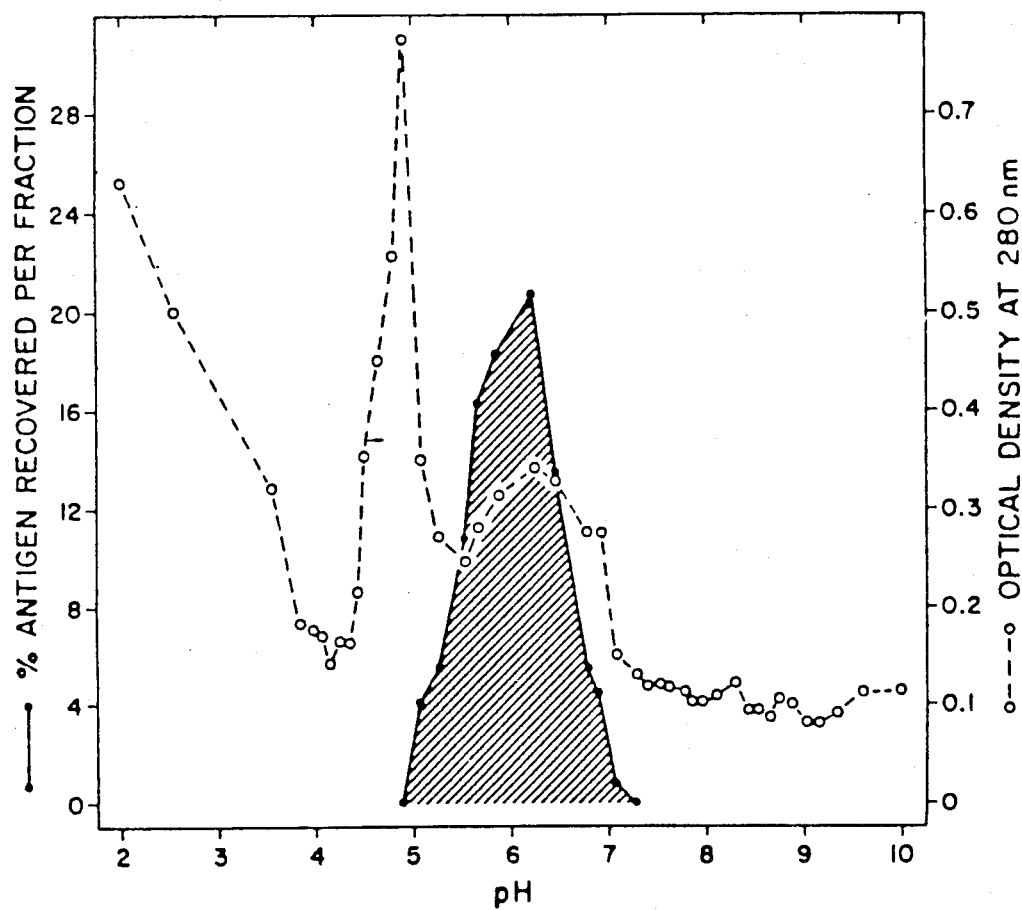
FIG. 3 is a graph of pH vs. antigen recovered per fraction and pH vs. optical density depicting isoelectric focusing of HTLV III antigens (prepared as described for FIG. 1). Fractions were tested by RIA at a 1:10 dilution and the relative amount of antigen detected was calculated from the calibration curve shown in FIG. 1.

Isoelectric focusing revealed that the major antigen detectable by RIA has an isoelectric point of approximately pH 6.2 (FIG. 3). The major portion (approximately 98%) of antigen failed to attach to columns of insolubilized Concanavalin A or lentil lectin, suggesting that this antigen is not a glycoprotein.

The described properties of the most abundant antigen detectable by RIA (or ELISA) indicate that this antigen corresponds to the major core protein of HTLV III (J. Schupbach et al., *Lancet*, 1, 303 (1984); Kitchen supra; S. Oroszlan and R. V. Gilden, *Immunochemistry of Viruses, The Basis For Serodiagnosis and Vaccines*, eds. M. H. V. Van Regenmortel and A. R. Neurath, Elsevier, Amsterdam, The Netherlands (1985)).

Example 2

Figure 4:
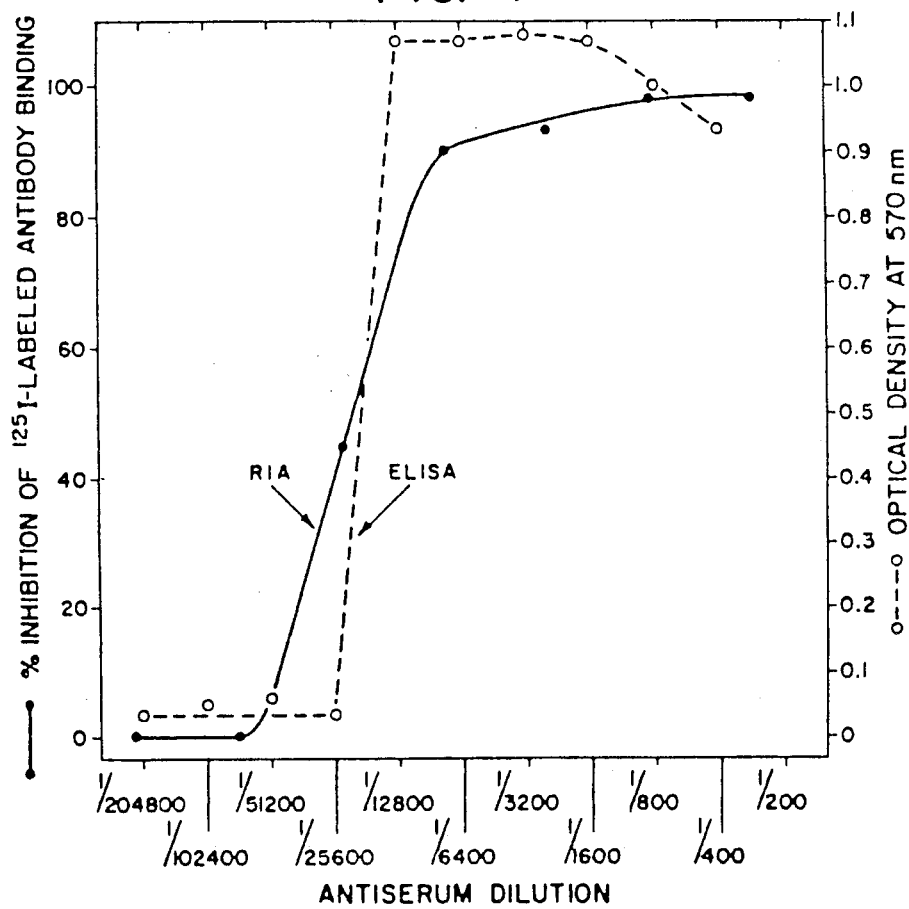
FIG. 4 shows a plot of antiserum dilution versus % inhibition of $^{125}I$-labeled antibody binding depicting the results of RIA-inhibition tests and antiserum dilution versus optical density showing the results of ELISA-inhibition tests with serial dilution of a human anti-HTLV III serum used as source for development of the described assays. It is noted that the inhibition of HTLV III antigen binding to anti-HTLV III IgG-coated wells in the ELISA test at decreasing anti-serum dilutions resulted in increasing optical density readings indicating a decreasing decolorization of the substrate due to diminished binding of beta-lactamase-conjugated anti-HTLV III to wells of the ELISA plates.
Figure 5:
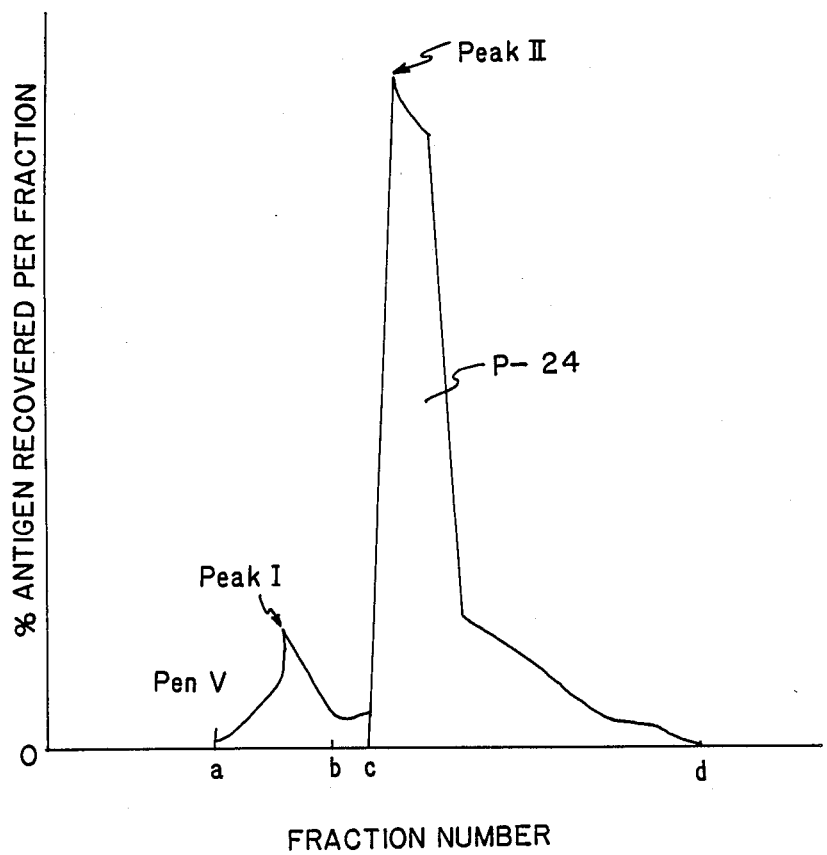
FIG. 5 is a schematic representation of a plot of antigen recovered per fraction vs. fraction number.

RIA and ELISA for anti-HTLV III P24 and application of these tests for screening of populations differing in risks of developing AIDS The RIA and ELISA for anti-HTLV III P24 is based on the inhibition by antibodies of attachment of the P24 antigen to the solid support. The adsorbed P24 is subsequently detected by $^{125}$I-labeled or beta-lactamase labeled anti-HTLV III. The endpoint titers of the antiserum which served as the source for antibody were similar for RIA and ELISA (FIG. 4).

Since the total volume of test samples in ELISA was 40% of that used in RIA, the absolute sensitivity for anti-HTLV III P24 was about the same for both tests. Since the dilution of the crude HTLV III antigen preparation in the inhibition assays is such that P24 is the only antigen detectable by RIA (or ELISA) (FIG. 2), the test is specific for anti-HTLV III P24. The presence of normal human serum in the diluent for the described assays minimizes the probability of finding specimens falsely positive for anti-HTLV III—a chronic problem with another test (S. H. Weiss, J. J. Goedert, M. G. Sarngadharan, A. J. Bodner, R. C. Gallo and W. A. Blattner, *JAMA*, 253, 221 (1985)). The standard deviation (SD) for counts obtained for negative controls was ±15% of the corresponding mean value, and the distribution of counts fitted a normal probability distribution. The 50% endpoints thus corresponded to reduction of control counts by 3.33×SD, suggesting a probability of $4 \times 10^{-4}$ for false positive samples (G. W. Snedecor and W. E. Cochran, *Statistical Methods* The Iowa State University Press, Ames, Iowa, (1971)).

The frequency of positive specimens among random voluntary blood donors was 2/600. The prevalence of anti-HTLV III P24 antibodies determined by RIA in populations at high risk of developing AIDS is shown in the Table below:

TABLE

Prevalence of antibodies to HTLV III core protein P24 in serum specimens collected from distinct donor groups

| Donors | Total Number | Number of positive specimens* | % of positives |
|---|---|---|---|
| Random voluntary blood donors | 600 | 2 | 0.33 |
| Hemophiliacs | 22 | 8 | 36.4 |
| Random homosexual males | 331 | 83 | 25.1 |
| Homosexual males with positive markers for Hepatitis B virus infection** | 40 | 20 | 50.0 |
| Homosexual males with chronic | 60 | 42 | 70.0 |

| TABLE-continued | | | |
|---|---|---|---|
| Prevalence of antibodies to HTLV III core protein P24 in serum specimens collected from distinct donor groups | | | |
| Donors | Total Number | Number of positive specimens* | % of positives |
| lymphadenopathy | | | |

*Determined by RIA
**Presence of hepatitis B surface antigen in serum

Homosexual males preselected on the basis of positive markers of infection with HBV had a higher prevalence of anti-HTLV III P24 antibodies as compared with random homosexual males, in accordance with observations that lifestyle risk factors for HBV (W. Szmuness, J. Med. Virol., 4, 327, (1979)) and HTLV III infections are similar (J. J. Goedert, R. J. Briggar, D. M. Winn, M. H. Greene, D. L. Mann, R. C. Gallo, M. G. Sarngadharan, S. H. Weiss, R. J. Grossman, A. J. Bodner, D. M. Strong and W. A. Blattner, Lancet, 2, 711 (1984)). The prevalence of these antibodies in hemophiliacs is similar to percentages described in other reports (R. Cheingsong-Popov, R. A. Weiss, A. Dalgleish, R. S. Tedder, D. J. Jeffries, D. C. Shannon, R. B. Ferns, E. M. Briggs, I. V. D. Weller, S. Mitton, M. W. Adler, C. Farthing, A. G. Lawrence, B. G. Gazzard, J. Weber, J. R. W. Harris, A. J. Pinching, J. Craske and J. A. J. Barbara, Lancet, 2, 477 (1984); B. L. Evatt, D. P. Francis, M. F. McLane, T. H. Lee, C. Cabradilla, S. F. Stein, D. N. Lawrence, J. S. McDougal, T. J. Spira, J. I. Mullens and M. Essex, Lancet, 2, 698 (1983); L. W. Kitchen, F. Barin, J. L. Sullivan, M. F. McLane, D. B. Brettler, P. H. Levine and M. Essex, Nature, 312, 367 (1984); M. Melbye, R. J. Briggar, J. C. Chermann, L. Montagnier, S. Stenbjerg and P. Ebbesen, Lancet, 2, 40 (1984); M. Melbye, R. Madhok, P. S. Sarin, G. D. O. Lowe, J. J. Goedert, K. S. Froebel, R. J. Briggar, S. Stenbjerg, C. D. Forbes, R. C. Gallo and P. Ebbesen, Lancet, 2, 1444 (1984).

Seventy-four specimens selected from distinct groups (see the above Table) were tested by ELISA and a concordance between ELISA and RIA test results was established, except that one of the two RIA-positive samples from random blood donors was negative in the ELISA test. This sample caused only a 68% inhibition of $^{125}$I-labeled antibody binding in RIA (compare with FIG. 4). The other specimen caused a 79% inhibition in RIA was positive by ELISA.

It will be appreciated that the instant specification and claims are set forth by way of illustration and not limitation, and that various modifications and changes may be made without departure from the spirit and scope of the present invention.

What is claimed is:

1. A process for the detection of antibodies to HTLV III/LAV comprising:
   (A) mixing an unknown serum sample with a crude HTLV III/LAV viral antigen selected from the group consisting of
   (1) an antigen prepared by
      (i) propagating HTLV III virus infected cells in a culture medium;
      (ii) separating the cells out of the medium of step (1)(i);
      (iii) precipitating proteins and virus out from the resultant medium of step (1)(ii);
      (iv) inactivating the virus from the product of step (1)(iii) and releasing P24 core protein and Penv protein; and
      (v) recovering P24 core protein and Penv protein;
   (2) a P24 antigen prepared by
      (i) propagating HTLV III/LAV virus infected cells in a culture medium;
      (ii) separating the cells out of the medium of step (2)(i);
      (iii) precipitating proteins and virus out from the resultant medium of step (2)(ii);
      (iv) inactivating and disrupting the virus from the product of step (2)(iii), and
      (v) separating out the HTLV III/LAV P24 antigen; and
   (3) a Penv antigen prepared by
      (i) propagating HTLV III/LAV virus infected cells in a culture medium;
      (ii) separating the cells out of the medium of step (3)(i);
      (iii) precipitating proteins and virus out from the resultant medium of step (3)(ii);
      (iv) inactivating and disrupting the virus from the product of step (3)(iii), and
      (v) separating out the HTLV III/LAV Penv antigen;
   (B) incubating the resultant mixture from step (A);
   (C) contacting the resultant mixture of step (B) with a solid substrate coated with antibody to HTLV III/LAV;
   (D) incubating the resultant mass from step (C);
   (E) washing the resultant mass from step (D);
   (F) contacting the resultant mass from step (E) with a labeled antibody to HTLV III/LAV;
   (G) incubating the resultant mass from step (F);
   (H) washing the resultant mass from step (G);
   (I) assaying the label in the resultant mass from step (H);
   (J) as a negative control, mixing a serum sample known to be negative to HTLV III/LAV antibody with a diluent;
   (K) subjecting the resultant mass from step (J) to steps (B) to (I);
   (L) as a positive control, mixing a predetermined amount of said crude HTLV III/LAV viral antigen and said diluent;
   (M) subjecting the resultant mass from step (L) to steps (B) to (I); and
   (N) comparing the results of the assay for the label from steps (I), (K) and (M).

2. A process according to claim 1, wherein said antibodies which bind to HTLV III/LAV are anti-P24 antibodies of HTLV III/LAV and said antigen is a P24 antigen.

3. A process according to claim 1, wherein said antibodies which bind to HTLV III/LAV are anti-Penv antibodies of HTLV III/LAV and said antigen is a Penv antigen.

4. A process according to claim 1, wherein said culture medium contains fetal calf serum.

5. A process according to claim 1, wherein the diluent contains fetal calf serum, human serum and a buffer.

6. A process according to claim 1, wherein the labeled antibody is a radio labeled or enzyme labeled antibody.

7. A process according to claim 1, wherein said inactivation and disruption is conducted by contacting the product of steps (1)(iii), (2)(iii) and (3)(iii) with polyoxyethylene derivatives of fatty acid partial esters of sorbitol anhydrides and tri-n-butylphosphate.

8. A process according to claim 1 wherein said separating out is by molecular exclusion chromatography.

9. A process according to claim 1, wherein said substrate is polystyrene beads.

10. A process according to claim 6, wherein said labeled antibodies to HTLV III are $^{125}$I-labeled anti-HTLV III antibodies.

11. A process according to claim 5, wherein said buffer is tris buffered saline.

12. A process according to claim 6, wherein said enzyme is beta-lactamase.

13. A process according to claim 1, wherein said solid substrate is one or more wells of microtiter plates.

* * * * *